US 6,447,987 B1
Sep. 10, 2002

(12) United States Patent
Hess et al.

(10) Patent No.: US 6,447,987 B1
(45) Date of Patent: Sep. 10, 2002

(54) PROLONGED STORAGE OF RED BLOOD CELLS (75) Inventors: John R. Hess, Bethesda, MD (US); Tibor J. Greenwalt, Cincinnati, OH (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/664,635

(22) Filed: Sep. 19, 2000

Related U.S. Application Data (63) Continuation-in-part of application No. 09/154,102, filed on Sep. 16, 1998, now Pat. No. 6,150,085.
(60) Provisional application No. 60/099,594, filed on Sep. 9, 1978, and provisional application No. 60/098,520, filed on Aug. 31, 1998.

(51) Int. Cl.[7] ................................................. A01N 1/02
(52) U.S. Cl. ........................................................... 435/2
(58) Field of Search ............................................. 435/2

(56) References Cited

U.S. PATENT DOCUMENTS 5,789,151 A * 8/1998 Bitensky et al. ................ 435/2
5,906,915 A * 5/1999 Payrat et al. .................... 435/2
6,150,085 A * 11/2000 Hess et al. ...................... 435/2

OTHER PUBLICATIONS

Mazor et al., "Prolonged Storage of Red Cells: The Effect of pH, Adenine and Phosphate", Vox Sang. 66:264–269 (1994).*

* cited by examiner

Primary Examiner—Sandra E. Saucier
(74) Attorney, Agent, or Firm—Elizabeth Arwine (57) ABSTRACT Novel additive solutions useful for the storage of human red blood cells (RBCs) under refrigerated conditions are disclosed. Also disclosed is a method of using the additive solutions in an appropriate volume to preserve RBCs at about 1 to 6° C. for up to at least about 11 weeks or more. Additive solutions and processes in accordance with the present invention allow the viable storage of human RBCs for an extended period of time in a solution which is directly infusible in humans.

12 Claims, 6 Drawing Sheets

FIG. 1

CHROMIUM-51, TECHNETIUM-99mm
24 HOUR RECOVERY STUDIES OF RBC'S
STORED IN EAS-61 (TABLE 1)

PROLONGED STORAGE OF RED BLOOD CELLS

CROSS-REFERENCE TO RELATED APPLICATIONS

This application is a continuation-in-part of application Ser. No. 09/154,102, filed Sep. 16, 1998, which is based on provisional application No. 60/099,594, filed on Sep. 9, 1998 and provisional application No. 60/098,520, filed Aug. 31, 1998. The contents of these documents is expressly incorporated herein.

STATEMENT REGARDING FEDERALLY SPONSORED RESEARCH OR DEVELOPMENT

This work was performed at the Hoxworth Blood Center, University of Cincinnati, Ohio, under Army contract DAMD17-95-C-5029, and at the Walter Reed Army Institute of Research, Silver Spring, Md.

BACKGROUND OF THE INVENTION

1. Field of Invention

The invention generally relates to methods and materials associated with the storage of whole blood and red blood cells (RBC).

2. Description of Related Art

Whole blood storage was first demonstrated by Rous & Turner in 1916 and Robertson in 1917. Acid-citrate-dextrose (ACD, 1943) and Citrate-phosphate-dextrose solution (CPD, 1957) were subsequently approved for 21-day storage of whole blood. CPD with adenine (CPDA-1, 1979) was later introduced and used for extending the shelf-life of stored whole blood and packed RBC for up to 5 weeks. Additive Solutions extended RBC storage to 6 weeks in 1981. Red blood cells (RBCs) stored in these solutions have shown steady deterioration after about 6 weeks as determined by the inability of 75% of such cells to survive in the circulation for 24 hours after reinfusion back into the human donor. It has been observed that during continued refrigerated storage, glucose is consumed at a decreasing rate, as the concentration of metabolic waste, i.e. lactic acid and hydrogen ions, increases. Such a decrease in the rate of glucose metabolism leads to depletion of adenosine triphosphate (ATP) which directly correlates to the recovery of RBCs when the cells are returned to the circulation.

The development of additive solutions for the preservation of red blood cells (RBCs) after their separation from whole blood has allowed the design of formulations which are specifically tailored to the needs of RBCs. Additive solutions such as Adsol® (AS-1), Nutricel® (AS-3), Optisol® (AS-5), and ErythroSol® were designed to extend the storage of RBCs at 1–6° C.

Almost all of the whole blood collected now is made into components, and the RBC fraction is stored as packed RBCs. For blood drawn into the additive solution systems, RBCs are packed by centrifugation, plasma is removed so that RBCs make up 80% of the volume, and then 100 ml of additive solution is added sterilely. The resulting suspensions have a RBC volume fraction of approximately 55%. RBCs stored in the conventional FDA-approved additive solutions can be stored for only 6 weeks with an acceptable 24-hour in vivo recovery.

To increase the time of acceptable in vivo recovery of RBCs in liquid storage, attempts have been made to improve additive solutions and storage processes. In "Studies In Red Blood Cell Preservation-7. In vivo and in vitro Studies With A Modified Phosphate-Ammonium Additive Solution," by Greenwalt et al., Vox. Sang. 65:87–94 (1993), the authors determined that the experimental additive solution (EAS-2) containing in mM: 20 $NH_4Cl$, 30 $Na_2HPO_4$, 2 adenine, 110 dextrose, 55 mannitol, pH 7.15, is useful in extending the storage shelf-life of human RBCs from the current standard of 5–6 weeks to an improved standard of 8–9 weeks. However, packed RBCs stored in the medium were not directly infusible but required the removal of the supernatant with a washing step prior to transfusion due to the presence of ammonium in the additive solution.

In "Studies in Red Blood Cell Preservation-8. Liquid Storage of Red Cells in Glycerol-Containing Additive Solution," Vox. Sang. 67:139–143 (1994), Greenwalt et al. described an Experimental Additive Solution 25 (EAS-25) that allowed 73 percent recovery of packed red cells at nine weeks. However, the resulting RBC units contained about 1 percent glycerol and thus, are not safe for transfusion in humans in massive amounts.

In "Extending the Storage of Red Cells at 4° C.," Transfus. Sci. 15:105–115 (1994) by Meryman et al., acceptable viability of RBCs stored in very dilute suspensions at low hematocrit for as long as 27 weeks were demonstrated. However, such stored RBC suspensions were not acceptable for direct infusion due to their high content of potassium and ammonia and their low volume fraction of RBCs.

Consequently, there remains a need for improved additive solutions and processes which increase the storage time of human RBCs over that of conventional solutions and processes while allowing the RBC storage suspension to be directly tranfusable into humans and maintaining an acceptable in vivo recovery of RBCs.

SUMMARY OF THE INVENTION

The present invention relates to a novel additive solution useful for the storage of human RBCs under refrigerated conditions using an additive solution to preserve RBCs at about 1 to 6° C. for up to about 11 weeks or more.

Additive solutions and processes in accordance with the present invention allow the viable storage of human RBCs for an extended period of time in a solution which is directly infusible in humans.

It is, therefore, an object of the present invention to provide an additive solution for storage of human RBCs which solution substantially increases the storage time of the RBCs at about 1 to about 6° C. while maintaining an acceptable recovery of the RBCs.

It is also an object of the present invention to provide an additive solution for storage of human RBCs which is physiologically safe and suitable for direct infusion into humans in massive amounts.

It is yet another object of the present invention to provide a method of storing human RBCs for about 11 weeks or more at about 1 to about 6° C. with an acceptable 24-hour in vivo fractional recovery of the RBCs.

It is also another object of the present invention to provide novel RBC storage suspensions which are directly infusible into humans following about 11 weeks or more storage at about 1 to about 6° C.

To achieve the foregoing and other objects in accordance with the purposes of the present invention, a novel additive solution for preserving RBCs was developed. The aqueous solution contains adenine, dextrose, $Na_2HPO_4$, mannitol, and at least one physiologically acceptable sodium salt in amounts sufficient to preserve RBCs which amount includes a buffering amount of sodium bicarbonate and or trisodium citrate to maintain the pH at or above about 8, preferably at about 8.4.

The additive solutions are useful in a method for storing RBCs, which method include the steps of:

(a) mixing a sample of whole blood containing the RBCs and plasma with an anticoagulant solution, forming thereby a suspension of whole blood;

(b) treating the whole blood suspension to separate the RBCs from the plasma, forming thereby packed RBCs;

(c) mixing the packed RBCs with an appropriate amount of an additive solution in accordance with the invention thereby forming a suspension of RBCs;

(d) cooling said suspension of RBCs to about 1 to about 6° C.; and (e) storing said cooled suspension of RBCs according to standard blood bank procedures for a period of about 11 weeks or more.

RBC suspensions produced in accordance with the invention after about 11 weeks or more of storage provide a sufficiently therapeutic amount of recoverable RBCs and are directly infusible into humans without further processing in accordance with known standards established for transfusion of RBCs.

BRIEF DESCRIPTION OF THE DRAWINGS

FIG. 3(A–D) demonstrates the effect of increasing concentrations of sodium bicarbonate on A) RBC ATP content, B) whole blood lactate content, C) extracellular pH, and D) intracellular pH. The individual solutions contain 0 (-♦-), 10 (-■-), 20 (-▲-), and 30 (-●-) mEq/L of sodium bicarbonate.

FIG. 4(A–D) demonstrates the effect of increasing concentrations of sodium chloride on A) RBC ATP content, B) extracellular pH, C) whole blood lactate content, and D) hemolysis %. The individual solutions contain 26 (-♦-), 50 (-■-), 100 (-▲-), and 150 (-●-) mEq/L of sodium chloride.

FIG. 5(A–E) compare the effects of storage in two different additive solutions at two volumes on A) RBC ATP content, B) extracellular pH, C) whole blood lactate content, D) morphology index and E) hemolysis %. The individual solutions and volumes were AS-3 at 100 mL (-○-), AS-3 at 200 mL (-●-), EAS-61 at 100 mL (-□-), and EAS-61 at 200 mL (-■-).

DETAILED DESCRIPTION OF THE INVENTION

For purposes of this invention, the term "recovery" is used herein to indicate the fraction of stored RBCs that remains in circulation for 24 hours, after re-infusion into the original human donor.

The term "prolonged" or "extended" storage is used herein to indicate the preservation or storage of RBCs for a period of time greater than 6 weeks up to about 11 weeks or more with an acceptable recovery of RBCs.

An additive solution in accordance with the invention comprises an aqueous solution of adenine, dextrose, $Na_2HPO_4$, mannitol, and at least one physiologically acceptable sodium salt, in concentrations suitable to preserve RBCs which amount includes the amount of sodium bicarbonate or trisodium citrate which would maintain the pH during storage at levels at or above about 8, preferably at levels about 8.4. In general, the solution contains adenine from about 1 to 3 mM, dextrose from about 20 to 115 mM, $Na_2HPO_4$ from about 4 to 15 mM, mannitol from about 15 to 60 mM, and at least one physiologically acceptable sodium salt from about 20 to 130 mM. Preferably, adenine is about 2 mM, dextrose is about 50 to 110 mM, $Na_2HPO_4$ is about 9 to 12 mM, mannitol is about 20 to 50 mM, and at least one physiologically acceptable sodium salt is about 25 to 75 mM. This amount would include the 10–30 mM of sodium bicarbonate. A combination of $Na_2HPO_4$, and $NaH_2PO_4$, can also be used in lieu of $Na_2HPO_4$, alone.

Suitable sodium salts useful in the medium of the invention include those salt compounds containing a sodium cation which are physiologically acceptable in humans. Preferred sodium salts include sodium chloride, sodium acetate, sodium citrate and the like. Most preferably, the medium contains about 20 to 100 mM of sodium chloride and 0 to 53 mM of sodium acetate. These preferred molar amounts would be lessened by the molar amount of sodium bicarbonate or trisodium citrate present.

The pH of the additive solution is maintained in a range of about 7 to 9 at room temperature. Preferably, the pH of the additive solution of the invention is in the range of about 8 to 8.8. Most preferably, the pH of the additive solution is about 8.4 to about 8.6.

The osmolarity of the suspension medium of the invention is in the range of about 200 to 310 mOsm. Preferably, the osmolarity is in the range of about 221 to 280 mOsm. Most preferably, the osmolarity of the additive solution is about 240 to 256 mOsm.

RBCs useful in the present invention are those which have been separated from their plasma and resuspended in an anticoagulant solution in the normal course of component manufacture. Briefly stated, a standard whole blood sample (450±45 ml) containing RBCs and plasma is mixed with an anticoagulation solution (about 63 ml) to form a suspension of whole blood. Proportional increases or decreases in solution volumes to reflect different donor blood volumes such as 400±40 ml–500±50 ml can also be used. The whole blood suspension is thereafter centrifuged to separate the RBCs from the blood plasma thereby forming a packed RBCs. The performance of the overall process is improved by leukocyte reduction using conventional techniques.

Suitable anticoagulants include conventional anticoagulants known for storage of RBCs. Preferably, the anticoagulants include citrate anticoagulants having a pH of 5.5 to 8.0, e.g. CPD, half-strength CPD and the like. The most preferred anticoagulant is CPD.

In accordance with the method of the invention, additive solution is added to the packed RBC suspension in an amount sufficient to provide a therapeutic effective amount of recoverable RBCs in the cell suspension. Preferably, the additive solution is added at a volume ranging from about 140 ml to about 400 ml, preferably about 180 to about 300 ml, most preferably about 300 ml.

The RBC volume fraction in the cell suspension, i.e. after addition of additive solution, is about 27 to 50% of the total suspension. More preferably, the RBC volume fraction in the cell suspension is about 35 to about 45%. most preferably, the RBC volume fraction in the cell suspension is about 43% of the total suspension.

The RBC suspension is then generally stored in standard polyvinyl chloride (PVC) blood storage bags using either the collection bag or PVC transfer packs of different sizes depending on the volume of the stored aliquot. The RBC suspension is stored at about 1 to 6° C. according to standard blood bank procedure as described in *Clinical-Practice of Blood Transfusion* editors: Petz & Swisher, Churchill-Livingston publishers, N.Y., 1981. All documents cited herein infra and supra are hereby incorporated by reference thereto.

Without being bound to any particular theory or explanation, it is believed that when stored in large volumes of additive solution in accordance with the invention, the increased volume of nutrient solution allows an increased mass of substrate to be delivered at acceptable concentrations while providing solute for dilution of metabolic waste products thereby reducing feedback inhibition of glucose metabolism.

It is further postulated that another feature of the additive solutions of the invention is that they produce swelling of the RBCs initially followed by a gradual reduction of red cell volume during storage. Such a process has been called "regulated volume decrease." It is hypothesized that during this process either the tyrosine phosphatase activity present in the RBC is suppressed or the tyrosine kinase is activated. Both of these enzymes have been demonstrated to be abundant in the membranes of these cells (Zipser, Y. and Kosower, N. S. (1996) *Biochem. J.* 314:881; Mallozzi C. et al. (1997) *FASEB J.* 11:1281). It is anticipated that the net phosphorylation of the band 3 protein in the RBC membrane would result in the release of phosphofructokinase, aldolase and glyceraldehyde-3-phosphate dehydrogenase in the cytoplasm from their bound state to band 3 (Harrison, M. L. et al. (1991) *J. Biol. Chem.* 266:4106; Cossins, A. R. and Gibson J. S. (1997) *J. Exper. Biol.* 200:343; Low, P. S. et al. (1993) *J. Biol. Chem.* 268:14627; Low, P. S. et al. (1995) *Protoplasma* 184:1961. The availability of these three enzymes in the glycolytic pathway would be expected to increase the metabolism of glucose by the RBC, thereby promoting acceptable levels of ATP levels in the RBCs.

The additive solutions of the invention can also be used to rehydrate lyophilized RBC or in the thawing of stored frozen blood or blood component, e.g. RBC.

It is understood that the examples and embodiments described herein are for illustrative purposes only and that various modifications or changes in light thereof are to be included within the spirit and purview of this application and the scope of the appended claims.

The following Materials and Methods were used in the Examples which follow.

Preparation of Additive Solution: Additive solutions in accordance with the present invention were prepared by mixing the components in an aqueous solution. Adenine was obtained from Sigma Chemical (St. Louis, Mo.). The other chemicals used were of USP grade and were obtained from Fisher Scientific (Cincinnati, Ohio). Sterility of the additive solution was achieved by filtration through a 0.22-um filter with a filling bell (Sterivex-GX, Millipore corporation, Bedford, Mass.) into a 1-L sterile transfer packs (Baxter Healthcare, IL). Sterility was established by culture.

The pH was measured using an Orion pH meter (Model 900A Analytical Technology, Inc., Orion, Boston, Mass.). The osmolalities were measured by freezing point depression (Osmette TM Precision Systems, Sudbury, Mass.).

Blood Samples: Blood donors acceptable by the American Association of Blood Banks and Food and Drug Administration criteria were used. Standard units of blood (450 ml) were collected with 63 ml CPD polyvinyl-chloride bags. Each unit of whole blood was centrifuged and the platelet-rich plasma expressed into a satellite bag. Additive solutions in the stated volume were added and the unit stored at 1–6° C. for the stated period.

In vivo testing: After storage, in vivo RBC recovery was measured 24 hours after autologous reinfusion using a double radioisotope procedure [Moroff, G. et al. (1984) *Transfusion* 24:109–114; International Committee on Standardization in Hematology. Recommended Method for Radioisotope RedCell Survival Studies. Brit. *J. Haematology* (1980) 45:659–6661. In brief, a sample of the stored blood was labeled with $^{51}$Cr. Concurrently, a fresh blood sample was collected from the volunteer and labeled with $^{99m}$Tc (Ultratag RBC kit f or the preparation of Technitium Tc-99m, labeled red blood cells package insert. Mallinckrodt Medical, St. Louis, Mo.). Carefully measured aliquots of the radiolabeled red cells were mixed and rapidly reinfused. Blood samples were collected at timed intervals during the 60 minutes immediately following the reinfusion and again at 24 hours. Radioactivity of the samples was measured in a gamma counter (Wallac CLINGAMMA Twin 2, Model 1272, Turku, Finland). Gamma emissions from $^{99m}$Tc radiolabeled cells were measured in the samples collected during the 30 minutes following reinfusion and used to determine an independent RBC volume. The activity from $^{51}$Cr labeled cells was measured in the delayed samples and used to calculate the recovery of the transfused RBCs. The results were expressed as 24-hour in vivo recovery percentage of RBC.

Storage solutions: The compositions of the various EAS and AS-3 (Nutricel, Pall Medical, Covina, Calif.) are compared in Table 2. The EASs were made from high purity adenine, sugars, and salts and sterilely filtered into one-liter storage bags. The bags were held at room temperature for two weeks. The solutions were then cultured and the cultures incubated for another two weeks. When sterility was confirmed by the absence of bacterial growth for 7–14 days, the solutions were aliquoted by weight into 600 mL bags. All connections were made using a sterile connecting device (SCD 312, Termumo Medical Corp. Elkton, Md.).

Study Design (Examples 4–6): Three "pooling" studies were conducted to evaluate RBC metabolism and physiology over an 11 week period. Pooling reduces the largest source of variability in conventional blood storage studies, e.g. different donors. The RBC units were grouped into sets of 4 ABO-matched units, each set was then pooled, mixed and realiquoted into identical pooled units.

Statistical Analysis

Comparisons of means of measured values at given times within the trials were evaluated with the analysis of variance using procedures that take account of the weekly repeated measures. Probabilities less likely than 0.05 were considered statistically significant.

EXAMPLE 1

RBC recovery after storage was measured as the autologous 24-hour recovery fraction. Whole blood stored in CPDA-1 for 5 weeks, packed red blood cells stored in CPDA- I for 5 weeks, packed red blood cells stored in AS-3 solution for 6 and 7 weeks, were compared to 7 to 8-week storage of packed red blood cells in EAS-61, an additive solution according to the present invention.

The components of EAS-61 are described in Table 1 below. The pH of the solution at room temperature was 8.58 and the measured total osmolarity was 256 mOsm/Kg $H_2O$.

TABLE 1

| Composition of EAS-61 additive solution | |
|---|---|
| Adenine | 2 mM |
| Dextrose | 110 mM |
| $Na_2HPO_4$ | 12 mM |
| Mannitol | 55 mM |
| NaCl | 26 mM |

Ten volunteers had their blood stored in additive solution EAS-61 for seven weeks and ten for eight weeks.

Figure 1:
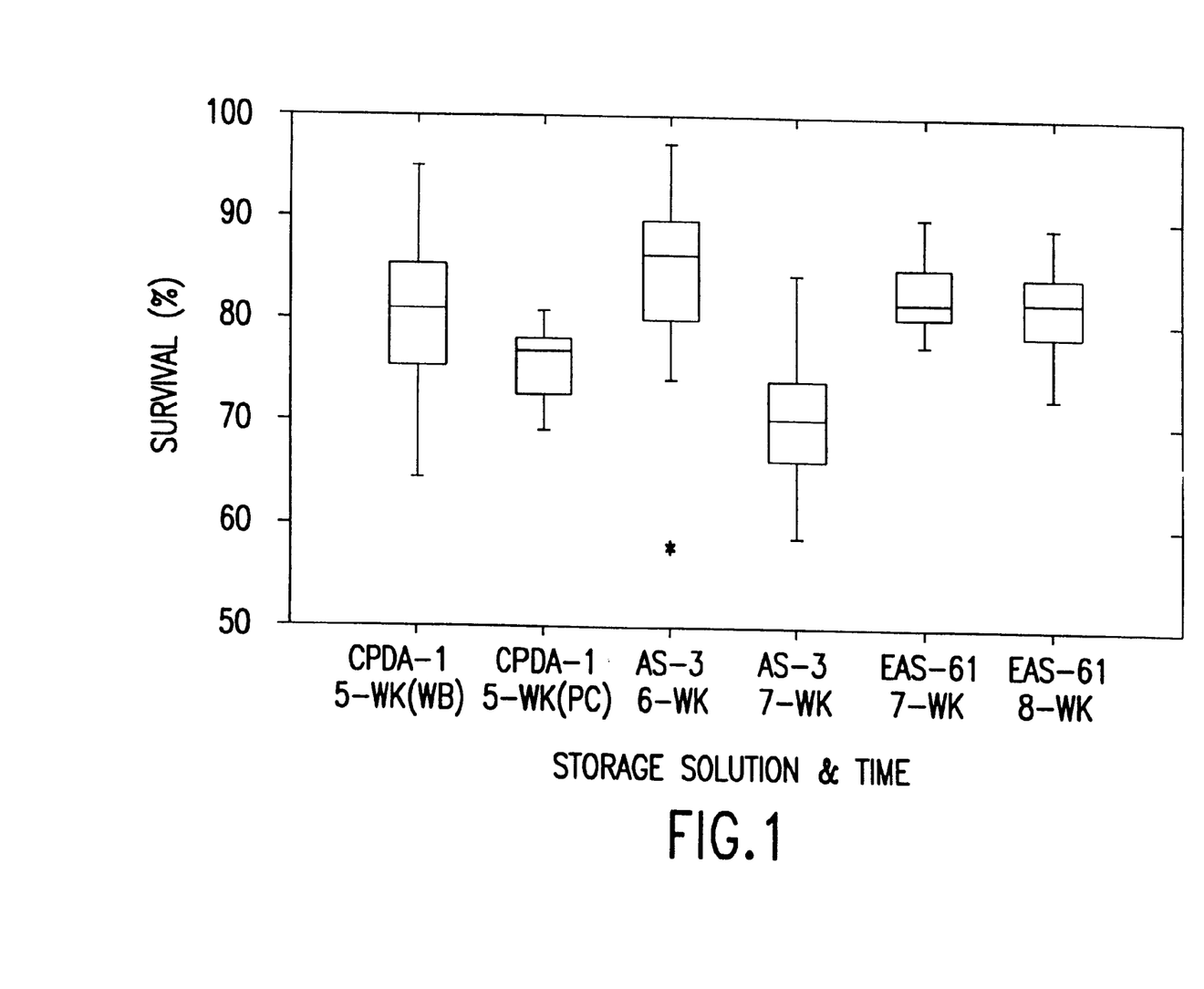
FIG. 1 demonstrates the 24 hour in vivo recovery of RBCs stored in a variety of original solutions for periods ranging from 5 to 8 weeks.

Results (shown in FIG. 1) indicate that 24-hour in vivo recovery percentage of RBC stored in 200 ml of the additive solution of the invention was over 80% after 7 and 8 weeks of storage. By comparison, percentage RBC recovery in 100 ml of AS-3 after 7 weeks of storage was less than about 70%, and in CPDA-I with no additive solution, less than 80% after only 5 weeks of storage of packed RBCs. Values for the licensed solutions are from the referenced literature found in the legend to FIG. 1.

EXAMPLE 2

The RBC recovery after storage for 8 and 9 weeks in EAS-61 was also determined. Two hundred milliliters of the additive solution was added to packed cells from one unit of blood and stored at 1 to 6° C. The results of in vivo testing of ten units at eight weeks and ten units at nine weeks were expressed as 24-hour in vivo recovery percentage of RBC and are recorded in FIG. 2.

Figure 2:
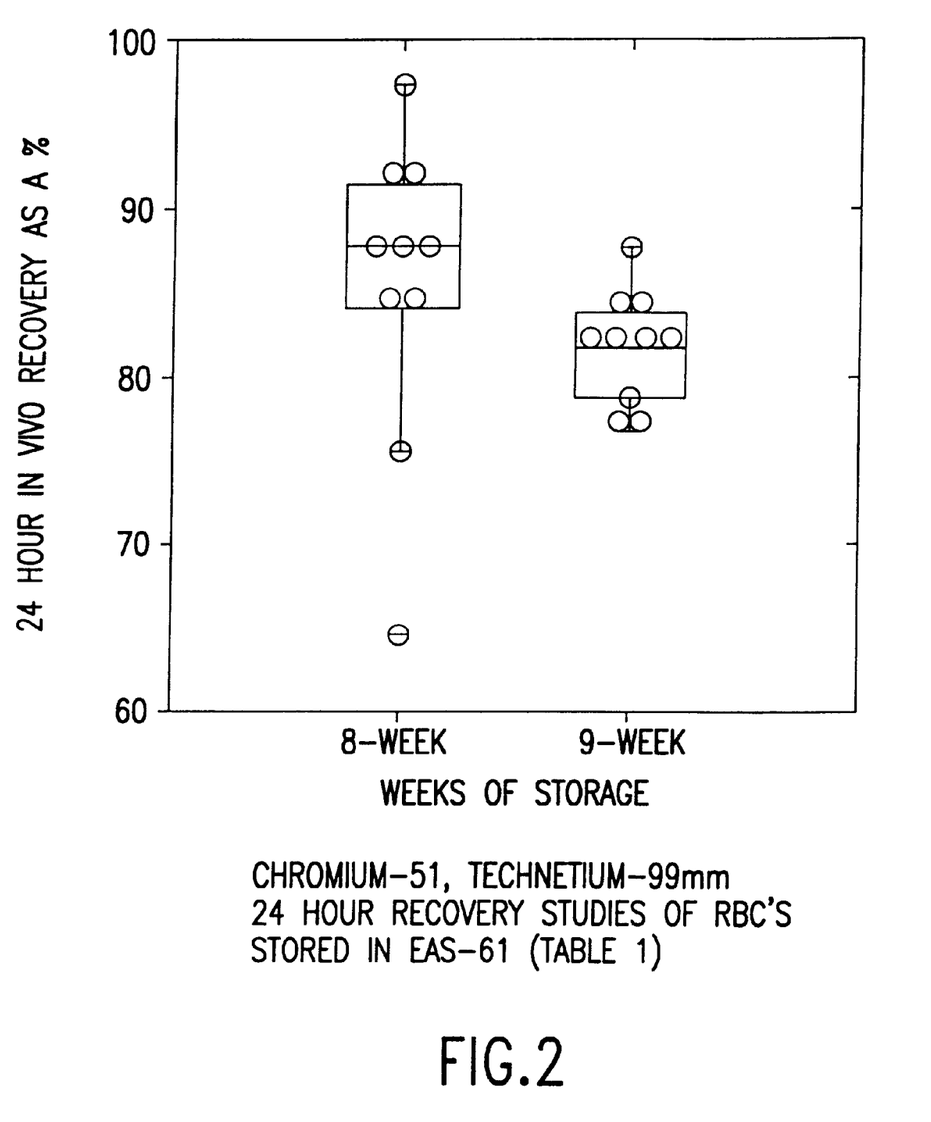
FIG. 2 demonstrates the 24 hour in vivo recovery of RBCs stored in EAS-61, an original additive solution according to the present invention, for periods ranging from 8 to 9 weeks.

As shown in FIG. 2, the percentage recovery of RBCs stored in 200 ml of the additive solution of the invention was 81% after 9 weeks of storage.

Results indicate that RBCs can be stored for at least nine weeks in 200 ml of additive solution according to the present invention with satisfactory in vivo recovery.

EXAMPLE 3

In this study, units were stored in variants of EAS-64 with increasing sodium bicarbonate concentrations (0, 10, 20, 30 mmol/L) but a constant total sodium concentration and a constant 300 mL AS volume. See Table 2, Study 1 for the components of the composition.

RBC Unit Preparation

EAS-64 variant units: Standard units (450±45 mL) of blood were collected from each donor into 63 mL of CPD anticoagulant in the primary polyvinyl-chloride (PVC) bag of an AS-1 triple-bag collection set (code 4R-14-36, Baxter Healthcare Corporation, Deerfield, Ill.). Packed cells were prepared by centrifugation at 5,000×g for 5 minutes at room temperature followed by the removal of sufficient plasma to achieve a hematocrit of 75–80%. ABO-matched PRBCs were then pooled in groups of three in 1 L sterile bags (code 4R-20-32, Baxter Healthcare Corporation, Deerfield, Ill.), mixed thoroughly, and aliquoted into the study units by weight using sterile tubing connection for all the transfers. The study units were produced in 600 mL transfer bags (code 4R-20-23, Baxter Healthcare Corporation, Deerfield, Ill.) by mixing the PRBC aliquot with 300 mL of the EAS.

In vitro Measurements

The total hemoglobin (HGB) concentration, WBC counts, and RBC counts were measured with a clinical hematology analyzer (MaxM Coulter Counter, Coulter Electronics, Hialeah, Fla.). Supernatant hemoglobin was measured using 3,3',5,5'-tetramethylbenzidine (procedure No. 527, Sigma diagnostics). The average degree of RBC shape change from discocytes to echinocytes to spherocytes was measured as RBC morphology indexes on 200 cells, determined according to the method of Usry, Moore, and Manalo. Percent hemolysis was determined by the ratio of free to total hemoglobin. The results were expressed as percent hemolysis to compensate for the differences in storage hematocrit and Hgb concentrations between samples. Centrifuged microhematocrits (Clay Adams, Becton-Dickinson, Rutherford, N.J.) were performed to prevent osmotic changes in cell volume caused by the isotonic diluent used in the blood analyzer. Mean corpuscular volumes (MCV) were calculated from the spun microhematocrit and the RBC count.

RBC ATP and whole blood lactate concentrations were measured in deproteinized supernatants. Whole blood or packed cell aliquots were mixed with cold 12% trichloracetic acid to precipitate blood proteins, centrifuged at 2700×g for 10 minutes, and the protein free supernatant frozen at −80° C. until tested. ATP was assayed enzymatically using a commercially available test kit (Procedure 366-UV, Sigma Diagnostics, St. Louis, Mo.).

Intra- and extracellular pH were measured with a benchtop pH meter (Orion 900A, Orion Research Inc., Boston, Mass.) at 22° C. Blood pH has a temperature coefficient of

TABLE 2

| | Composition of the additive solutions used | | | | | | | | | |
|---|---|---|---|---|---|---|---|---|---|---|
| | Study 1 | | | | Study 2 | | | | Study 3 | |
| Name | EAS-64 | EAS-65 | EAS-66 | EAS-67 | EAS-61 | EAS-71 | EAS-72 | EAS-73 | AS-3 | EAS-61 |
| Volume (mL) | 300 | 300 | 300 | 300 | 200 | 200 | 200 | 200 | 100/200 | 100/200 |
| NaCl | 75 | 65 | 55 | 45 | S26 | 50 | 100 | 150 | 70 | 26 |
| $NaHCO_3$ | 0 | 10 | 20 | 30 | 0 | 0 | 0 | 0 | 0 | 0 |
| $NaH_2PO_4$ | 0 | 0 | 0 | 0 | 0 | 0 | 0 | 0 | 23 | 0 |
| $Na_2HPO_4$ | 9 | 9 | 9 | 9 | 12 | 12 | 12 | 12 | 0 | 12 |
| Adenine | 2 | 2 | 2 | 2 | 2 | 2 | 2 | 2 | 2 | 2 |
| Dextrose | 50 | 50 | 50 | 50 | 110 | 110 | 110 | 110 | 55 | 110 |
| Mannitol | 20 | 10 | 20 | 20 | 50 | 50 | 50 | 50 | 0 | 50 |
| pH | 8.4 | 8.4 | 8.4 | 8.4 | 8.4 | 8.4 | 8.4 | 8.4 | 5.8 | 8.4 |

All concentrations in mmol/L

−0.015 pH units/° C., so pH measured at 22° C. will be about 0.22 pH units higher than pH measured at 37° C.

Supernatant potassium, glucose, and inorganic phosphorus testing was sent to an outside laboratory (Health Alliance Laboratories, Cincinnati, Ohio) (here and in example 5).

RBC ATP and phosphate concentrations were measured in deproteinized packed cells and whole blood respectively. Whole blood or packed cell aliquots were mixed with cold 10% trichloroacetic acid to precipitate blood proteins, centrifuged at 2700×g for 10 minutes, and the protein free supernatant frozen at −80° C. until tested. ATP was assayed enzymatically using a commercially available test kit (Procedure 366-UV, Sigma Diagnostics, St. Louis, Mo.). Inorganic phosphate was measured using a procedure by Boehringer-Mannheim Corp., that involves the formation of ammonium phosphomolybdate (Hitachi 747-200).

Blood gases and pH were measured on a blood gas analyzer (Coming 855, Ithaca, N.Y.). pH was measured at 37° C. Phosphate, lactate, and glucose were measured on a programmable chemical analyzer (Hitachi 902, Boehringer-Mannheim Corp., Indianapolis, Ind.).

Results

Figure 3:
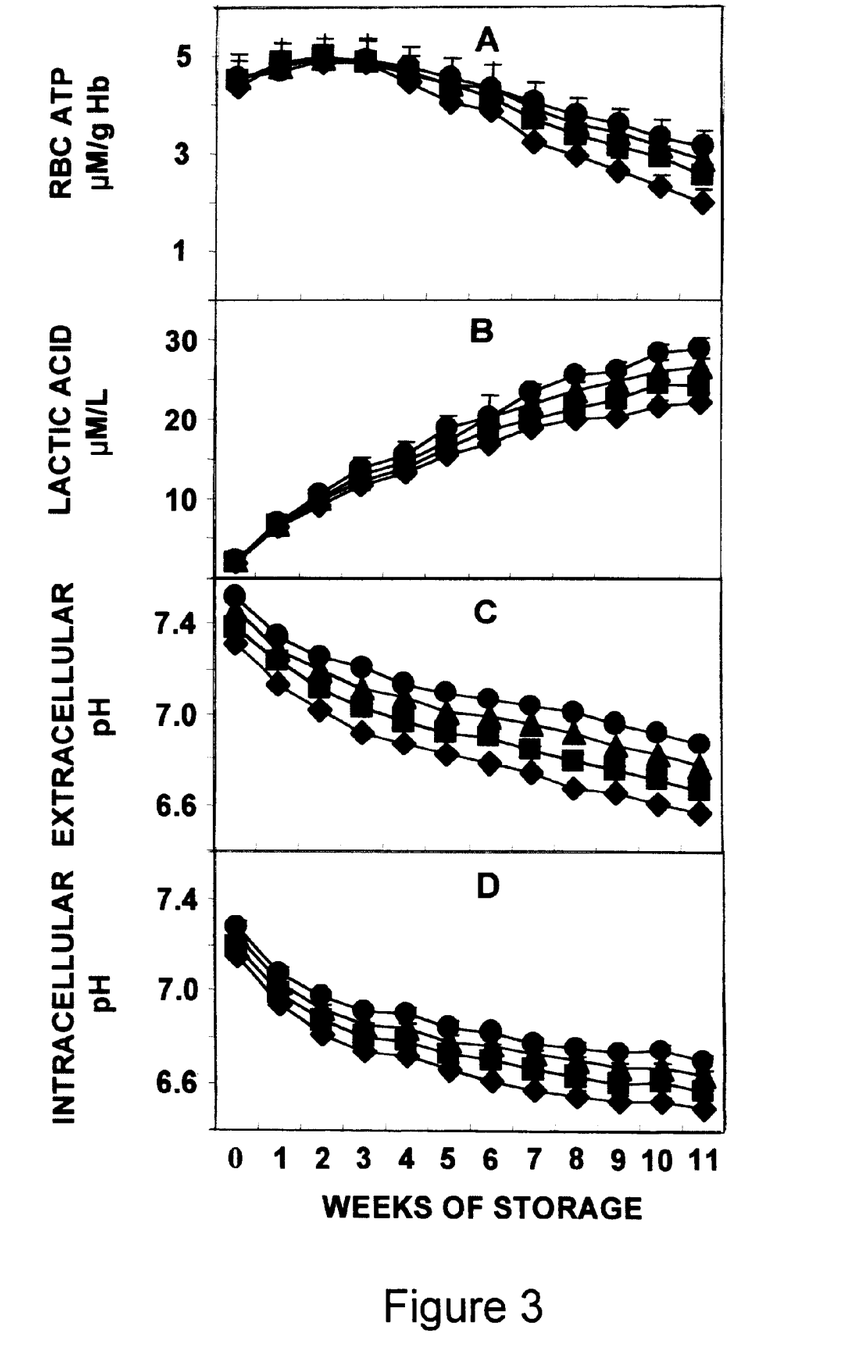

Replacement of sodium chloride by sodium bicarbonate was associated, in a dose-dependent manner, with increased RBC ATP concentrations at the end of storage (FIG. 3A). the increases in RBC ATP concentrations were temporally associated with increased glucose consumption (data not shown) and increased lactate production (FIG. 3B). This increased rate of glycolysis occurred in cells stored in solutions with a higher extracellular pH (FIG. 3C), which in turn resulted in a higher intracellular pH (FIG. 3D). There was no significant difference in RBC morphology or hemolysis with storage in the different solutions (data not shown).

EXAMPLE 4

In this study, units were stored in variants of EAS-61 with increasing sodium chloride concentrations (26, 50, 100, 150 mmol/L) but at a constant 200 mL AS volume. See Table 2, Study 2 for the components of the composition.

RBC Unit Preparation

EAS-61 variant units: Standard units (450±45 mL) of blood were collected from each donor into 63 mL of CPD anticoagulant in the primary polyvinyl-chloride (PVC) bag of an AS-1 triple-bag collection set (code 4R-14-36, Baxter Healthcare Corporation, Deerfield, Ill.). Packed cells were prepared by centrifugation at 5,000×g for 5 minutes at room temperature followed by the removal of sufficient plasma to achieve a hematocrit of 75–80%. ABO-matched PRBCs were then pooled in groups of four in 1 L sterile bags (code 4R-20-32, Baxter Healthcare Corporation, Deerfield, Ill.), mixed thoroughly, and aliquoted into the study units by weight using sterile tubing connection for all the transfers. The study units were produced in 600 mL transfer bags (code 4R-20-23, Baxter Healthcare Corporation, Deerfield, Ill.) by mixing the PRBC aliquot with 200 mL of the EAS.

In vitro Measurements

The total hemoglobin (HGB) concentration, WBC counts, and RBC counts were measured with a clinical hematology analyzer (MaxM Coulter Counter, Coulter Electronics, Hialeah, Fla.). Supernatant hemoglobin was measured using 3,3',5,5'-tetramethylbenzidine (procedure No. 527, Sigma diagnostics). The average degree of RBC shape change from discocytes to echinocytes to spherocytes was measured as RBC morphology scores on 200 cells, determined according to the method of Usry, Moore, and Manalo. Percent hemolysis was determined by the ratio of free to total hemoglobin. The results were expressed as percent hemolysis to compensate for the differences in storage hematocrit and Hgb concentrations between samples. Centrifuged microhematocrits (Clay Adams, Becton-Dickinson, Rutherford, N.J.) were performed to prevent osmotic changes in cell volume caused by the isotonic diluent used in the blood analyzer. Mean corpuscular volumes (MCV) were calculated from the spun microhematocrit and the RBC count.

RBC ATP and whole blood lactate concentrations were measured in deproteinized supernatants. Whole blood or packed cell aliquots were mixed with cold 12% trichloracetic acid to precipitate blood proteins, centrifuged at 2700×g for 10 minutes, and the protein free supernatant frozen at −80° C. until tested. ATP was assayed enzymatically using a commercially available test kit (Procedure 366-UV, Sigma Diagnostics, St. Louis, Mo.).

Blood gases and pH were measured in the second study on a blood gas analyzer (Coming 855, Ithaca, N.Y.). Thus, pH was measured at 37° C.

The total hemoglobin concentration, WBC counts, and RBC counts were measured with a different clinical hematology analyzer, but the same use of the spun microhematocrit was used to correct for cell swelling (Hematology Cell Counter System Series 9110+, Baker, Allentown, Pa.). Supernatant Hb was measured spectrophotometrically using a modified Drabkin assay.

RBC ATP and phosphate concentrations were measured in deproteinized packed cells and whole blood respectively. Whole blood or packed cell aliquots were mixed with cold 10% trichloroacetic acid to precipitate blood proteins, centrifuged at 2700×g for 10 minutes, and the protein free supernatant frozen at −80° C. until tested. ATP was assayed enzymatically using a commercially available test kit (Procedure 366-UV, Sigma Diagnostics, St. Louis, MO). Inorganic phosphate was measured using a procedure by Boehringer-Mannheim Corp., that involves the formation of ammonium phosphomolybdate (Hitachi 747-200).

Blood gases and pH were measured on a blood gas analyzer (Corning 855, Ithaca, N.Y.). pH was measured at 37° C. Phosphate, lactate, and glucose were measured on a programmable chemical analyzer (Hitachi 902, Boehringer-Mannheim Corp., Indianapolis, Ind.).

Results

Figure 4:
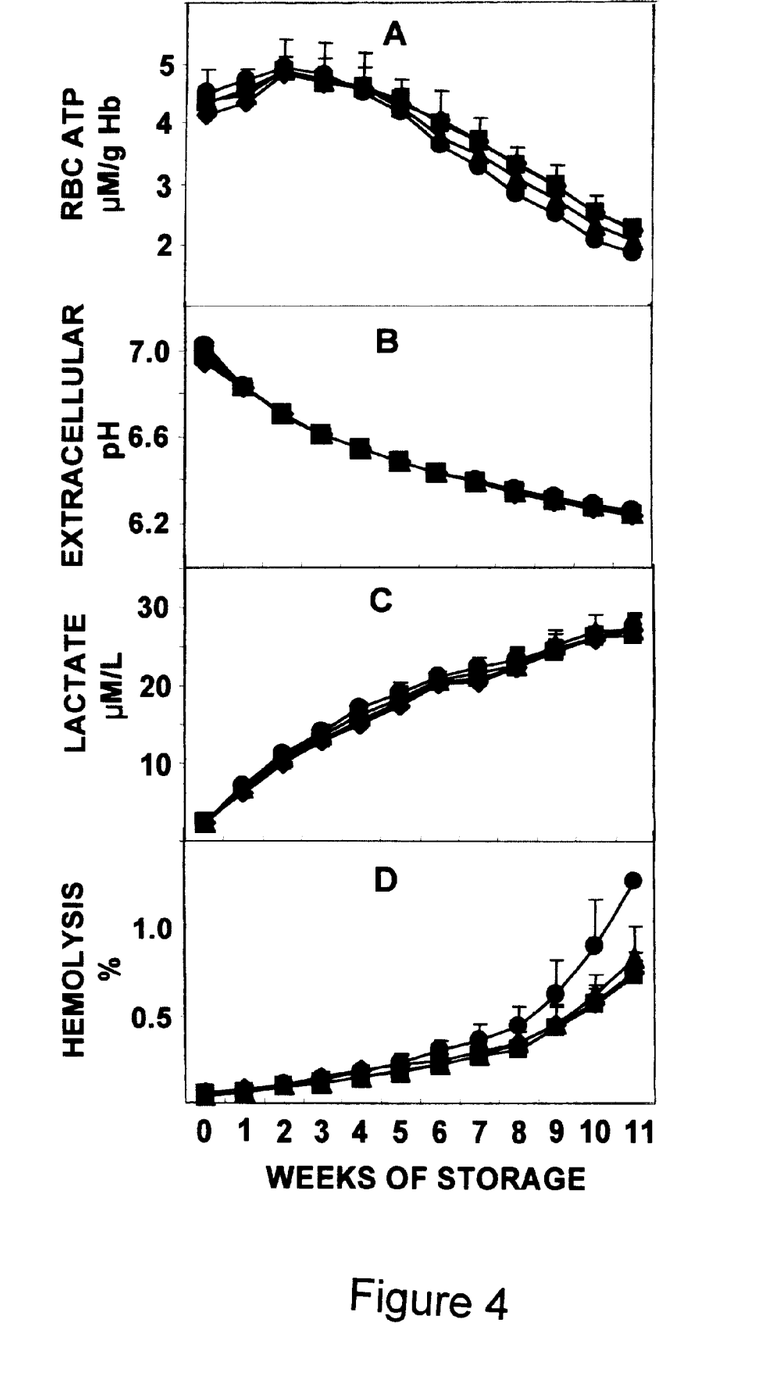

Successive increases of sodium chloride concentration were associated with decreases in mean cell volume, decreases in the RBC morphologic index, and increasing amounts of shed microvesicle protein in the storage supernatant (Table 3 (Table 2 in paper)). The decrease in RBC ATP concentration was statistically significant only for the highest dose (Table 3 and FIG. 4A). This change in RBC ATP concentration was not associated with any change in extracellular pH (FIG. 4B) or lactate production (FIG. 4C). At the highest sodium concentration, there was increased hemolysis in the last two weeks of storage (FIG. 4D).

TABLE 3

Outcomes of Study 2 after 9 weeks storage

| EAS-61 variants with increasing NaCl content | EAS-61 26 mEq of NaCl | EAS-71 50 mEq of NaCl | EAS-72 100 mEq of NaCl | EAS-73 150 mEq of NaCl |
| --- | --- | --- | --- | --- |
| MCV fL | 105.5 ± 3.2 | 100.4 ± 2.1 | 93.4 ± 2.1 | 88.5 ± 2.1 |
| Morphology Index | 81.1 ± 7.8 | 72.1 ± 9.4 | 61.2 ± 10.6 | 53.8 ± 12.3 |
| Vesicle Protein mg/dL RBCs | 8.7 ± 1.7 | 13.6 ± 1.9 | 26.7 ± 5.1 | 40.4 ± 7.8 |
| Hemolysis % | .78 ± .11 | .73 ± .10 | .84 ± .18 | 1.28 ± .33 |
| ATP % of initial | 53 ± 5 | 54 ± 5 | 50 ± 6 | 45 ± 4 |

EXAMPLE 5

In this study, units were stored in 100 and 200 mL of AS-3 and 100 and 200 ml of EAS-61. See Table 2, Study 3 for compositions employed. Electrolytes, pH, metabolites, RBC morphology scores and RBC ATP concentrations were measured weekly during storage using sterile sampling techniques.

RBC Unit Preparation

AS-3 and EAS-61 units: Standard units (450±45 mL) of blood were collected from each donor into 63 mL of CP2D anticoagulant in the primary polyvinyl-chloride (PVC) bag of an AS-3 double-bag collection set (code 762-54, Pall Corp, Covina, Calif.). Packed cells were prepared by centrifugation at 5,000×g for 5 minutes at room temperature followed by the removal of sufficient plasma to achieve a hematocrit of 75–80%. Four units of identical ABO type were then pooled and realiquoted as described above, and either 100 or 200 mL of AS-3 or 100 or 200 mL of EAS-61 was added.

All units were gently mixed by inversion 10 times, sampled aseptically for in vitro testing, and placed in refrigerated storage (1–6° C.) four hours or less after collection.

RBC ATP and phosphate concentrations were measured in deproteinized packed cells and whole blood respectively. Whole blood or packed cell aliquots were mixed with cold 10% trichloroacetic acid to precipitate blood proteins, centrifuged at 2700×g for 10 minutes, and the protein free supernatant frozen at −80° C. until tested. ATP was assayed enzymatically using a commercially available test kit (Procedure 366-UV, Sigma Diagnostics, St. Louis, Mo.). Inorganic phosphate was measured using a procedure by Boehringer-Mannheim Corp., that involves the formation of ammonium phosphomolybdate (Hitachi 747-200).

Blood gases and pH were measured on a blood gas analyzer (Corning 855, Ithaca, N.Y.). pH was measured at 37° C. Phosphate, lactate, and glucose were measured on a programmable chemical analyzer (Hitachi 902, Boehringer-Mannheim Corp., Indianapolis, Ind.).

Results

Figure 5:
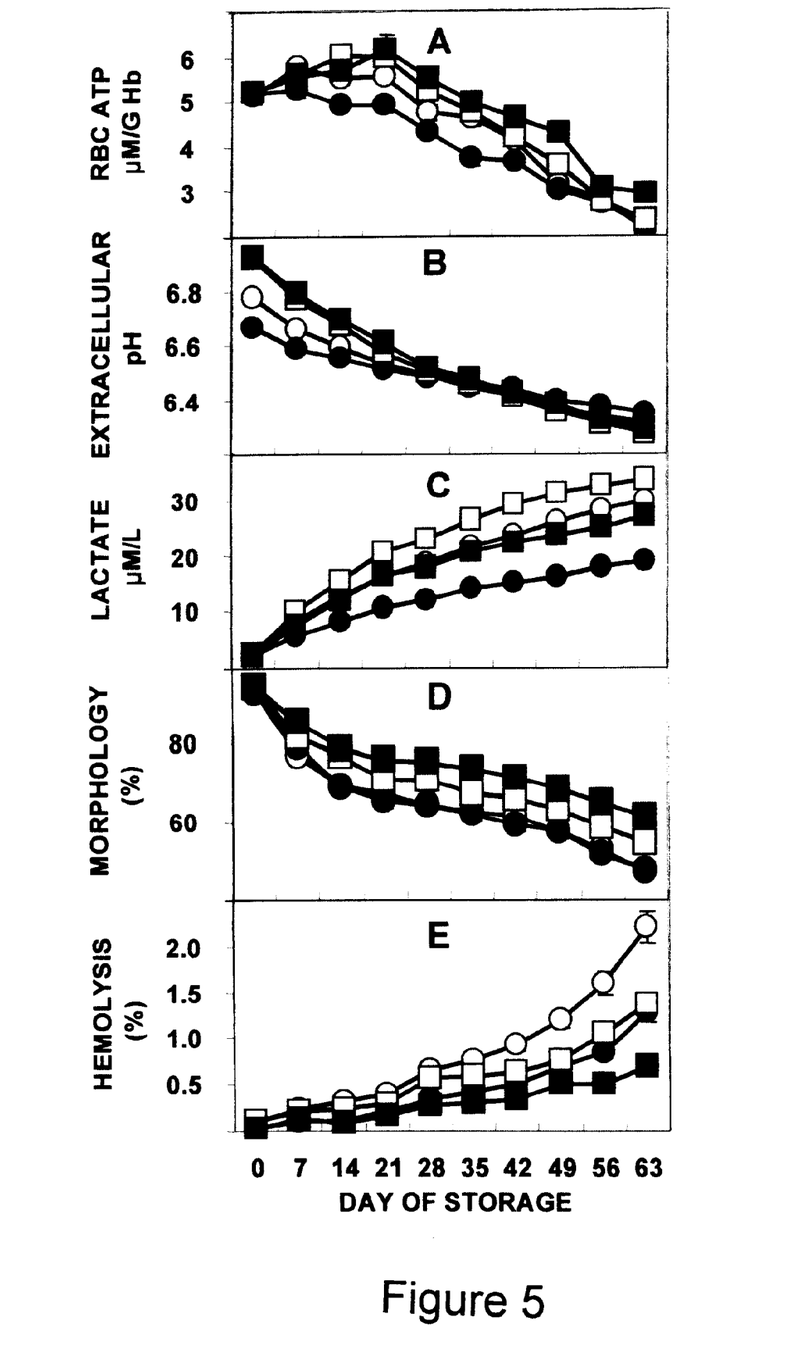
Figure 6:
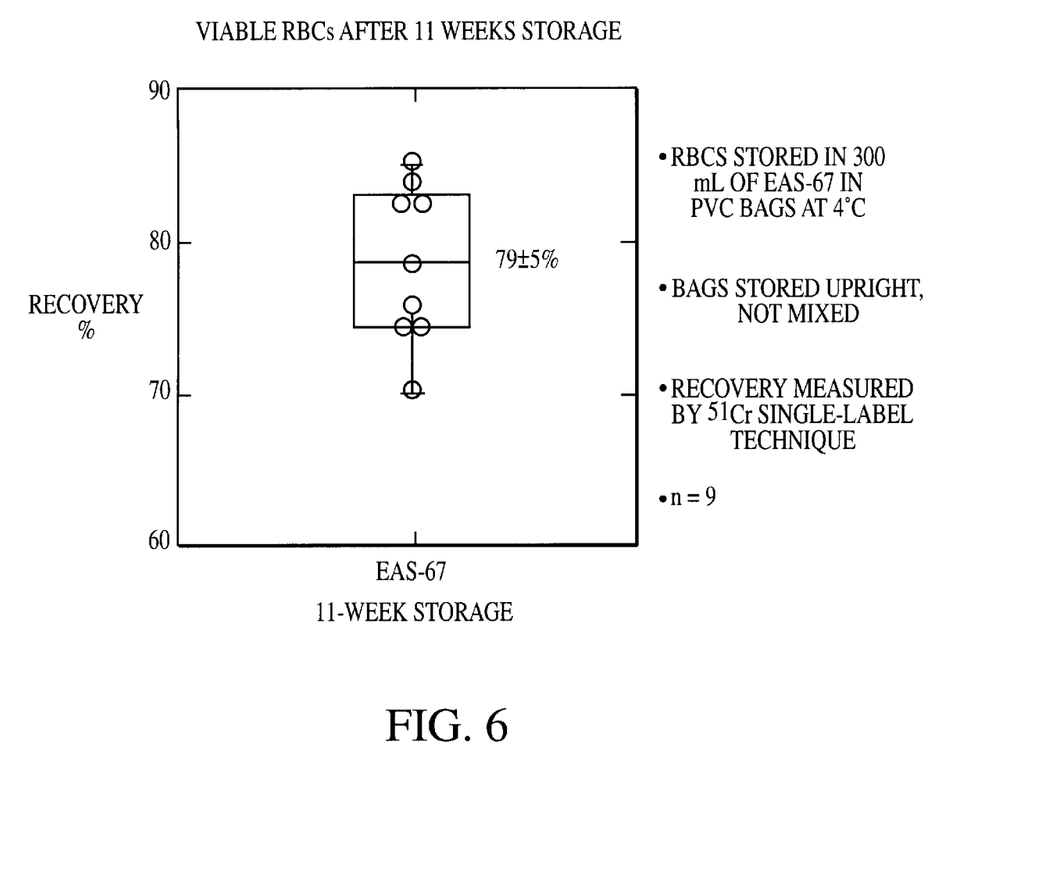
FIG. 6 shows the percentage recovery for EAS-67 additive after an 11-week storage.

EAS-61, an alkaline additive solution, caused RBC ATP concentrations to increase during the first three weeks of storage (FIG. 5A). This increase was less with 100 mL of AS-3 and did not occur with 200 mL of AS-3 (FIG. 5A). These increased concentrations in RBC ATP were temporally associated with increased supernatant pH (FIG. 5B) and increased lactate production (FIG. 5C). After the pHs of the suspending solutions became equivalent at 4 weeks of storage, the rates of lactate production, indicated by the slopes of the lactate concentration plots in FIG. 3C, became parallel. However, storage in EAS-61 was associated with better RBC morphology, and 200 mL of this additive was better than 100 mL (FIG. 5D). Hemolysis was reduced in EAS-61 compared to AS-3 and the 200 mL volume of each additive solution was better than the 100 mL volume in this regard (FIG. 5E).

Discussion

In Example 3, EAS-64, a 300 mL 10-week additive solution, was modified by the substitution of sodium chloride with sodium bicarbonate in amounts of 0, 10, 20 and 30 mMol/L. The addition of this salt of a strong base and weak acid makes the solutions more basic initially. The removal of protons in the carbonic anhydrase reaction and subsequent loss of carbon dioxide by diffusion through the bag keeps the solutions relatively more basic throughout storage (data on supernatant bicarbonate and $Pco_2$ not shown). Lactic acid was produced continuously during storage but at a decreasing rate with time in all the variants of the solution (FIG. 3B). With increasing amounts of bicarbonate the rate of lactic acid production was increasing better maintained during the course of storage so that at the end of storage the solution containing 30 mMol/L of bicarbonate contained 25% more lactate. This increased glycolytic activity was associated with increased RBC ATP concentrations after the third week of storage. RBC ATP content is the difference between ATP synthesis and ATP use. The rising ATP concentrations in the first two weeks of storage indicate a uniform excess of synthesis in all the solutions. The decreasing concentrations after the third week, a net ATP breakdown. If the rate of ATP synthesis is tied to the rate of glycolysis and the rate of breakdown is relatively constant, then the data show how solution pH can be manipulated to maintain RBC energetics especially at the end of storage.

In Example 5, EAS-61, a 200 mL 9-week additive solution, was modified by the addition of sodium chloride so that the resulting solutions had final concentrations of 26, 50, 100, and 150 mMol/L. The addition of sodium chloride had no effect on supernatant pH or the rate of lactate formation, but it did abolish cell swelling and led to greater morphologic change, greater loss of membrane microvesicles, and increased overall hemolysis. At the highest salt concentration the RBC ATP contents were less at the end of storage, suggesting that the shape change and membrane loss were energy consuming processes.

In Example 6, EAS-6 1 was compared directly with AS-3 at 100 and 200 mL additive volumes. The EAS-61 has higher pH but the AS-3 has a higher phosphate concentration giving it more buffer capacity. Increasing amounts of AS-3 drove the storage solution pH down, reducing lactate production and preventing the initial rise in RBC ATP concentration. By four weeks of storage, the supernatant pH of all the groups was equal and the rate of lactate production became essentially equal. Nevertheless, RBCs stored in the hypotonic EAS-61 solution had better morphology and 200 mL was better than 100 mL in this regard. Both solutions showed reduced hemolysis with increasing storage solution volume, but at each volume hemolysis was approximately half in EAS-61 of that observed in AS-3.

The experimental additive solutions (EAS-61, EAS-64 and EAS-67) appear to work to improve storage in several ways. In Example 4, they raise the pH in the storage solution and therefore in the intracellular space. The higher intercellular pH appears to drive glycolysis and therefore ATP synthesis in the early weeks of storage so that the later phase of declining RBC ATP content starts higher and later in the course of storage. In Example 5, relative osmotic hypotonia causes RBC swelling, which in turn improves the morphology and reduces the membrane loss by microvesiculation. The shape change and microvesiculation appear to be energy requiring processes and minimizing them appears to conserve ATP for other uses. In Example 6, as observed previously, increasing the volume of additive solution reduces the hemolysis in all the solutions tested.

What is claimed is:

1. An additive solution for prolonged storage of red blood cells (RBCs) at about 1 to 6° C. for a period of 11 weeks or more, said solution consisting essentially of adenine at about 1 to 3 mM, dextrose at about 20 to 115 mM, $Na_2HPO_4$, at about 4 to 15 mM, mannitol at about 15 to 60 mM, sodium chloride, sodium bicarbonate, and optionally another physiologically acceptable sodium salt wherein 1) the sodium bicarbonate is present in an amount sufficient to impart to the additive solution a pH from about 8.4 to about 9 and to maintain a pH of a RBC-additive solution suspension at levels above about 6.4 for an 11 week storage period, which formed suspension is suitable for direct infusion and 2) the additive solution has an osmolarity of about 200 to about 310.

2. The additive solution of claim 1 wherein, said solution has as osmolarity of about 221 to about 280 mOsm.

3. The additive solution of claim 2 wherein the osmolarity is about 240 to 256 mOsm.

4. The additive solution of claim 1 wherein the solution pH is about 8.0 to about 8.8.

5. The additive solution of claim 4 wherein the solution pH is about 8.4 to 8.6.

6. A method of preserving red blood cells (RBCs) for an extended period of time comprising:
   (a) mixing a sample of whole blood containing the RBCs to be stored and plasma with an anticoagulant solution, forming thereby a suspension of whole blood;
   (b) treating the whole blood suspension to concentrate the RBCs from the plasma, forming thereby packed RBCs;
   (c) mixing the packed RBCs with an appropriate amount of an additive solution comprising adenine at about 1 to 3 mM, dextrose at about 4 to 15 mM, mannitol at about 15 to 60 mM, and about 20–130 mM of a physiologically acceptable sodium salt, wherein a portion of the sodium salt is sodium chloride and sodium bicarbonate, present in a buffering amount, said solution having an osmolarity of about 200 to about 310 mOsm and a pH of about 8 to about 9, thereby forming a suspension of RBCs having about 25 to about 50% RBCs of the total suspension volume;
   (d) cooling said suspension of RBCs to about 1 to about 6° C.; and
   (e) storing said cooled suspension of RBCs according to standard bank procedures for a period of about 9 to about 11 weeks or more and at a pH above about 6.2.

7. The method of claim 6 wherein the solution osmolarity is about 221 to 280 mOsm.

8. The method of claim 7 wherein the solution osmolarity is about 240 to 256 mOsm.

9. The method of claim 6 wherein the solution pH is about 8.4 to 8.8.

10. The method of claim 9 wherein the solution pH is about 8.4 to 8.6.

11. The method of claim 9 wherein the volume percentage of RBCs in the RBC suspension is about 35 to about 45 of the total suspension.

12. A directly infusible red blood cells (RBCs) -additive solution suspension comprising RBCs suspended in the additive solution, wherein the additive solution has a pH between about 8.4 and about 9 and consists essentially of adenine at about 1 to 3mM, dextrose at about 20 to 115 mM, $Na_2HPO_4$ at about 4 to 15 mM, mannitol at about 15 to 60 mM, and other physiological acceptable sodium salts, wherein 1) a portion of the other sodium salt(s) are sodium chloride and sodium bicarbonate, 2) the volume fraction of RBCs suspended in the solution is 25 to 50% of the total solution, 3) an osmolarity of the additive solution is about 200 to about 310 and 4) the suspension is capable of being stored for about 11 weeks at a temperature of about 1 to about 6° C., 5) the pH of the suspension is about 6.2 or above during storage and 6) the in vivo RBCs recovery rate is above about seventy-five percent as measured by $^{51}Cr$ label technology.

* * * * *

UNITED STATES PATENT AND TRADEMARK OFFICE
CERTIFICATE OF CORRECTION

PATENT NO.    : 6,447,987 B1                                    Page 1 of 1
DATED         : September 10, 2002
INVENTOR(S)   : John R. Hess and Tibor J. Greenwalt It is certified that error appears in the above-identified patent and that said Letters Patent is hereby corrected as shown below:

<u>Title page,</u>
Item [60], should read:
-- [60]   Provisional application No. 60/099,594, filed on September 9, 1998, and provisional application No. 60/098,520, filed on August 31, 1998 --

Signed and Sealed this

Tenth Day of December, 2002

JAMES E. ROGAN
*Director of the United States Patent and Trademark Office*